United States Patent [19]

Wang et al.

[11] Patent Number: 5,108,922

[45] Date of Patent: Apr. 28, 1992

[54] DNA SEQUENCES ENCODING BMP-1 PRODUCTS

[75] Inventors: Elizabeth A. Wang, Carlisle; John M. Wozney, Hudson; Vicki Rosen, Brookline, all of Mass.

[73] Assignee: Genetics Institute, Inc., Cambridge, Mass.

[21] Appl. No.: 561,496

[22] Filed: Jul. 31, 1990

Related U.S. Application Data

[63] Continuation of Ser. No. 179,101, Apr. 8, 1988, abandoned, which is a continuation-in-part of Ser. No. 31,846, Mar. 26, 1987, Pat. No. 4,877,564, which is a continuation-in-part of Ser. No. 943,532, Dec. 17, 1986, abandoned, which is a continuation-in-part of Ser. No. 880,776, Jul. 1, 1986, abandoned.

[30] Foreign Application Priority Data

Jun. 30, 1987 [US]  United States .. PCT/US87/01537

[51] Int. Cl.$^5$ ................. C12N 15/06; C12N 15/12; C12P 19/34; C12P 21/02; C07H 15/12

[52] U.S. Cl. .................... 435/240.2; 435/252.33; 435/172.3; 435/320.1; 435/69.1; 435/252.3; 536/27; 935/9; 935/29; 935/32; 935/72; 935/11

[58] Field of Search ................ 435/320, 252.33, 172.3, 435/91, 69.1, 70.3, 240.2, 320.1; 530/300, 350; 514/12; 536/27

[56] References Cited

U.S. PATENT DOCUMENTS

| | | | |
|---|---|---|---|
| 4,468,464 | 8/1984 | Cohen et al. | 435/320 |
| 4,608,199 | 8/1986 | Caplan et al. | |
| 4,681,763 | 7/1987 | Nathanson | |
| 4,727,028 | 2/1988 | Santerre et al. | 435/240.2 |
| 4,795,804 | 1/1989 | Urist | 530/350 |
| 4,810,691 | 3/1989 | Seyedin et al. | 514/2 |

Primary Examiner—Jacqueline Stone
Assistant Examiner—Christopher S. F. Low
Attorney, Agent, or Firm—Ellen J. Kapinos; Bruce M. Eisen

[57] ABSTRACT

Purified BMP-1 proteins and processes for producing them are disclosed. They may be used in the treatment of bone and cartilage defects and in wound healing and related tissue repair.

8 Claims, 6 Drawing Sheets

FIGURE 1

```
      280           290       (1)              308                      323
CCTTGCCTCT TCTCTCTCCA GCT GCC TTC CTT GGG GAC ATC GCC CTG GAC GAG GAG
                     Ala Phe Leu Gly Asp Ile Ala Leu Asp Glu Glu 338                     353                     368
GAC TTG AGG GCC TTC CAA GTG CAG CAG GCT GCG GAC CTC AGA CAG CGT GCA ACC
Asp Leu Arg Ala Phe Gln Val Gln Gln Ala Ala Asp Leu Arg Gln Arg Ala Thr 383                 398     (37)          414         424
CGC AGG TCT TCC ATC AAA GCT GCA GGTACACTGG GTACAGGCCA
Arg Arg Ser Ser Ile Lys Ala Ala
```

FIGURE 2

```
       3419         3429         3439  (1)            3454
     CAGCCCTGGC TTCTTCTTTT CTCTTTAGCT GCC TTT CTT GGG GAC ATT GCC CTG GAC
                                      Ala Phe Leu Gly Asp Ile Ala Leu Asp 3469                      3484                3499                   3514
GAA GAG GAC CTG AGG GCC TTC CAG GTA CAG CAG GCT GTG GAT CTC AGA CGG CAC
Glu Glu Asp Leu Arg Ala Phe Gln Val Gln Gln Ala Val Asp Leu Arg Arg His 3529                  3544   (37)    3560          3570
ACA GCT CGT AAG TCC TCC ATC AAA GCT GCA GGTAAGCCGG GTGCCAATGG
Thr Ala Arg Lys Ser Ser Ile Lys Ala Ala
```

FIGURE 3

```
          10         20         30        (1)                50
CTAGAGGCCG CTTCCCTCGC CGCCGCCCCG CCAGC ATG CCC GGC GTG GCC CGC CTG CCG
                                       MET Pro Gly Val Ala Arg Leu Pro 65                  80                  95                 110
CTG CTG CTC GGG CTG CTG CTG CTC CCG CGT CCC GGC CGG CCG CTG GAC TTG GCC
Leu Leu Leu Gly Leu Leu Leu Leu Pro Arg Pro Gly Arg Pro Leu Asp Leu Ala 125                 140                 155
GAC TAC ACC TAT GAC CTG GCG GAG GAG GAC GAC TCG GAG CCC CTC AAC TAC AAA
Asp Tyr Thr Tyr Asp Leu Ala Glu Glu Asp Asp Ser Glu Pro Leu Asn Tyr Lys 170              185   (51)                200                 215
GAC CCC TGC AAG GCG GCT GCC TTT CTT GGG GAC ATT GCC CTG GAC GAA GAG GAC
Asp Pro Cys Lys Ala Ala Ala Phe Leu Gly Asp Ile Ala Leu Asp Glu Glu Asp 230                 245                 260                 275
CTG AGG GCC TTC CAG GTA CAG CAG GCT GTG GAT CTC AGA CGG CAC ACA GCT CGT
Leu Arg Ala Phe Gln Val Gln Gln Ala Val Asp Leu Arg Arg His Thr Ala Arg 290    (87)      305                 320
AAG TCC TCC ATC AAA GCT GCA GTT CCA GGA AAC ACT TCT ACC CCC AGC TGC CAG
Lys Ser Ser Ile Lys Ala Ala Val Pro Gly Asn Thr Ser Thr Pro Ser Cys Gln 335                 350                 365                 380
AGC ACC AAC GGG CAG CCT CAG AGG GGA GCC TGT GGG AGA TGG AGA GGT AGA TCC
Ser Thr Asn Gly Gln Pro Gln Arg Gly Ala Cys Gly Arg Trp Arg Gly Arg Ser 395                 410                 425
CGT AGC CGG CGG GCG GCG ACG TCC CGA CCA GAG CGT GTG TGG CCC GAT GGG GTC
Arg Ser Arg Arg Ala Ala Thr Ser Arg Pro Glu Arg Val Trp Pro Asp Gly Val 440                 455                 470                 485
ATC CCC TTT GTC ATT GGG GGA AAC TTC ACT GGT AGC CAG AGG GCA GTC TTC CGG
Ile Pro Phe Val Ile Gly Gly Asn Phe Thr Gly Ser Gln Arg Ala Val Phe Arg 500                 515                 530                 545
CAG GCC ATG AGG CAC TGG GAG AAG CAC ACC TGT GTC ACC TTC CTG GAG CGC ACT
Gln Ala MET Arg His Trp Glu Lys His Thr Cys Val Thr Phe Leu Glu Arg Thr 560                 575                 590
GAC GAG GAC AGC TAT ATT GTG TTC ACC TAT CGA CCT TGC GGG TGC TGC TCC TAC
Asp Glu Asp Ser Tyr Ile Val Phe Thr Tyr Arg Pro Cys Gly Cys Cys Ser Tyr 605                 620                 635                 650
GTG GGT CGC CGC GGC GGG GGC CCC CAG GCC ATC TCC ATC GGC AAG AAC TGT GAC
Val Gly Arg Arg Gly Gly Gly Pro Gln Ala Ile Ser Ile Gly Lys Asn Cys Asp
```

FIGURE 3 (CON'T)

```
              665                   680                   695
AAG TTC GGC ATT GTG GTC CAC GAG CTG GGC CAC GTC GTC GGC TTC TGG CAC GAA
Lys Phe Gly Ile Val Val His Glu Leu Gly His Val Val Gly Phe Trp His Glu 710                   725                   740                   755
CAC ACT CGG CCA GAC CGG GAC CGC CAC GTT TCC ATC GTT CGT GAG AAC ATC CAG
His Thr Arg Pro Asp Arg Asp Arg His Val Ser Ile Val Arg Glu Asn Ile Gln 770                   785                   800                   815
CCA GGG CAG GAG TAT AAC TTC CTG AAG ATG GAG CCT CAG GAG GTG GAG TCC CTG
Pro Gly Gln Glu Tyr Asn Phe Leu Lys MET Glu Pro Gln Glu Val Glu Ser Leu 830                   845                   860
GGG GAG ACC TAT GAC TTC GAC AGC ATC ATG CAT TAC GCT CGG AAC ACA TTC TCC
Gly Glu Thr Tyr Asp Phe Asp Ser Ile MET His Tyr Ala Arg Asn Thr Phe Ser 875                   890                   905                   920
AGG GGC ATC TTC CTG GAT ACC ATT GTC CCC AAG TAT GAG GTG AAC GGG GTG AAA
Arg Gly Ile Phe Leu Asp Thr Ile Val Pro Lys Tyr Glu Val Asn Gly Val Lys 935                   950                   965
CCT CCC ATT GGC CAA AGG ACA CGG CTC AGC AAG GGG GAC ATT GCC CAA GCC CGC
Pro Pro Ile Gly Gln Arg Thr Arg Leu Ser Lys Gly Asp Ile Ala Gln Ala Arg 980                   995                   1010                  1025
AAG CTT TAC AAG TGC CCA GCC TGT GGA GAG ACC CTG CAA GAC AGC ACA GGC AAC
Lys Leu Tyr Lys Cys Pro Ala Cys Gly Glu Thr Leu Gln Asp Ser Thr Gly Asn 1040                  1055                  1070                  1085
TTC TCC TCC CCT GAA TAC CCC AAT GGC TAC TCT GCT CAC ATG CAC TGC GTG TGG
Phe Ser Ser Pro Glu Tyr Pro Asn Gly Tyr Ser Ala His MET His Cys Val Trp 1100                  1115                  1130
CGC ATC TCT GTC ACA CCC GGG GAG AAG ATC ATC CTG AAC TTC ACG TCC CTG GAC
Arg Ile Ser Val Thr Pro Gly Glu Lys Ile Ile Leu Asn Phe Thr Ser Leu Asp 1145                  1160                  1175                  1190
CTG TAC CGC AGC CGC CTG TGC TGG TAC GAC TAT GTG GAG GTC CGA GAT GGC TTC
Leu Tyr Arg Ser Arg Leu Cys Trp Tyr Asp Tyr Val Glu Val Arg Asp Gly Phe 1205                  1220                  1235
TGG AGG AAG GCG CCC CTC CGA GGC CGC TTC TGC GGG TCC AAA CTC CCT GAG CCT
Trp Arg Lys Ala Pro Leu Arg Gly Arg Phe Cys Gly Ser Lys Leu Pro Glu Pro 1250                  1265                  1280                  1295
ATC GTC TCC ACT GAC AGC CGC CTC TGG GTT GAA TTC CGC AGC AGC AGC AAT TGG
Ile Val Ser Thr Asp Ser Arg Leu Trp Val Glu Phe Arg Ser Ser Ser Asn Trp 1310                  1325                  1340                  1355
GTT GGA AAG GGC TTC TTT GCA GTC TAC GAA GCC ATC TGC GGG GGT GAT GTG AAA
Val Gly Lys Gly Phe Phe Ala Val Tyr Glu Ala Ile Cys Gly Gly Asp Val Lys
```

FIGURE 3 (CON'T)

```
              1370             1385                  1400
AAG GAC TAT GGC CAC ATT CAA TCG CCC AAC TAC CCA GAC GAT TAC CGG CCC AGC
Lys Asp Tyr Gly His Ile Gln Ser Pro Asn Tyr Pro Asp Asp Tyr Arg Pro Ser 1415             1430             1445            1460
AAA GTC TGC ATC TGG CGG ATC CAG GTG TCT GAG GGC TTC CAC GTG GGC CTC ACA
Lys Val Cys Ile Trp Arg Ile Gln Val Ser Glu Gly Phe His Val Gly Leu Thr 1475             1490            1505
TTC CAG TCC TTT GAG ATT GAG CGC CAC GAC AGC TGT GCC TAC GAC TAT CTG GAG
Phe Gln Ser Phe Glu Ile Glu Arg His Asp Ser Cys Ala Tyr Asp Tyr Leu Glu 1520             1535              1550              1565
GTG CGC GAC GGG CAC AGT GAG AGC AGC ACC CTC ATC GGG CGC TAC TGT GGC TAT
Val Arg Asp Gly His Ser Glu Ser Ser Thr Leu Ile Gly Arg Tyr Cys Gly Tyr 1580             1595             1610               1625
GAG AAG CCT GAT GAC ATC AAG AGC ACG TCC AGC CGC CTC TGG CTC AAG TTC GTC
Glu Lys Pro Asp Asp Ile Lys Ser Thr Ser Ser Arg Leu Trp Leu Lys Phe Val 1640             1655             1670
TCT GAC GGG TCC ATT AAC AAA GCG GGC TTT GCC GTC AAC TTT TTC AAA GAG GTG
Ser Asp Gly Ser Ile Asn Lys Ala Gly Phe Ala Val Asn Phe Phe Lys Glu Val 1685             1700             1715             1730
GAC GAG TGC TCT CGG CCC AAC CGC GGG GGC TGT GAG CAG CGG TGC CTC AAC ACC
Asp Glu Cys Ser Arg Pro Asn Arg Gly Gly Cys Glu Gln Arg Cys Leu Asn Thr 1745             1760             1775
CTG GGC AGC TAC AAG TGC AGC TGT GAC CCC GGG TAC GAG CTG GCC CCA GAC AAG
Leu Gly Ser Tyr Lys Cys Ser Cys Asp Pro Gly Tyr Glu Leu Ala Pro Asp Lys 1790             1805             1820             1835
CGC CGC TGT GAG GCT GCT TGT GGC GGA TTC CTC ACC AAG CTC AAC GGC TCC ATC
Arg Arg Cys Glu Ala Ala Cys Gly Gly Phe Leu Thr Lys Leu Asn Gly Ser Ile 1850             1865             1880             1895
ACC AGC CCG GGC TGG CCC AAG GAG TAC CCC CCC AAC AAG AAC TGC ATC TGG CAG
Thr Ser Pro Gly Trp Pro Lys Glu Tyr Pro Pro Asn Lys Asn Cys Ile Trp Gln 1910             1925             1940
CTG GTG GCC CCC ACC CAG TAC CGC ATC TCC CTG CAG TTT GAC TTC TTT GAG ACA
Leu Val Ala Pro Thr Gln Tyr Arg Ile Ser Leu Gln Phe Asp Phe Phe Glu Thr 1955             1970             1985             2000
GAG GGC AAT GAT GTG TGC AAG TAC GAC TTC GTG GAG GTG CGC AGT GGA CTC ACA
Glu Gly Asn Asp Val Cys Lys Tyr Asp Phe Val Glu Val Arg Ser Gly Leu Thr 2015             2030             2045
GCT GAC TCC AAG CTG CAT GGC AAG TTC TGT GGT TCT GAG AAG CCC GAG GTC ATC
Ala Asp Ser Lys Leu His Gly Lys Phe Cys Gly Ser Glu Lys Pro Glu Val Ile
```

FIGURE 3 (CON'T)

```
      2060                 2075                 2090                      2105
ACC TCC CAG TAC AAC AAC ATG CGC GTG GAG TTC AAG TCC GAC AAC ACC GTG TCC
Thr Ser Gln Tyr Asn Asn MET Arg Val Glu Phe Lys Ser Asp Asn Thr Val Ser 2120                 2135                 2150                 2165
AAA AAG GGC TTC AAG GCC CAC TTC TTC TCA GAA AAG AGG CCA GCT CTG CAG CCC
Lys Lys Gly Phe Lys Ala His Phe Phe Ser Glu Lys Arg Pro Ala Leu Gln Pro 2180                 2195                 2210
CCT CGG GGA CGC CCC CAC CAG CTC AAA TTC CGA GTG CAG AAA AGA AAC CGG ACC
Pro Arg Gly Arg Pro His Gln Leu Lys Phe Arg Val Gln Lys Arg Asn Arg Thr
     (730)
      2225       2235       2245       2255       2265       2275       2285
CCC CAG TGAGGCCTGC CAGGCCTCCC GGACCCCTTG TTACTCAGGA ACCTCACCTT GGACGGAATG
Pro Gln 2295       2305       2315       2325       2335       2345       2355
    GGATGGGGGC TTCGGTGCCC ACCAACCCCC CACCTCCACT CTGCCATTCC GGCCCACCTC CCTCTGGCCG 2365       2375       2385       2395       2405       2415       2425
    GACAGAACTG GTGCTCTCTT CTCCCCACTG TGCCCGTCCG CGGACCGGGG ACCCTTCCCC GTGCCCTACC 2435       2445       2455       2465       2475       2485       2495
    CCCTCCCATT TTGATGGTGT CTGTGACATT TCCTGTTGTG AAGTAAAAGA GGGACCCCTG CGTCCTGCCT

CTAGA
```

DNA SEQUENCES ENCODING BMP-1 PRODUCTS

This application is a continuation of U.S. Ser. No. 179,101 filed Apr. 8, 1988 now abandoned which is a continuation-in-part of U.S. Ser. No. 31,346, filed Mar. 26, 1987, now U.S. Pat. Nos. 4,877,864; 943,332 filed Dec. 17, 1986 now abandoned; and 880,776 filed Jul. 1, 1986 now abandoned. This application also claims priority of PCT/US87/01537 filed Jun. 30, 1987.

The present invention relates to a novel family of purified proteins designated BMP-1 proteins and processes for obtaining them. These proteins (wherein BMP is bone morphogenic protein) may be used to induce bone and/or cartilage formation and in wound healing and tissue repair.

BMP-1 proteins are produced by culturing a cell transformed with a cDNA substantially as shown in Table III and recovering from the culture medium a protein containing substantially the 37 amino acid sequence as shown in Table II.

Some members of the BMP-1 protein family are further characterized by the ability of 200 nanograms of the BMP-1 protein to score at least +2 in the Rosen-modified Sampath-Reddi assay of bone and/or cartilage formation.

The bovine BMP-1 or bBMP-1 is a member of the family of the BMP-1 proteins of the invention. It contains substantially the amino acid sequence represented by amino acid #1 through amino acid #37 of Table I. Bovine BMP-1 is further characterized by the ability of 200 nanograms of this protein to score at least +2 in the Rosen-modified Sampath-Reddi assay of bone and/or cartilage formation.

Another aspect of the invention provides pharmaceutical compositions containing a therapeutically effective amount of a BMP-1 protein in admixture with a pharmaceutically acceptable vehicle or carrier. The compositions may be used for bone and/or cartilage formation BMP-1 compositions may also be used for wound healing and tissue repair. Compositions of the invention may further include at least one other therapeutically useful agent such as the BMP proteins BMP-2A, BMP-2B, and BMP-3 disclosed respectively in co-owned, and concurrently filed U.S. patent applications Ser. No. 179,100 and Ser. No. 179,197. Other therapeutically useful agents include growth factors such as epidermal growth factor (EGF), fibroblast growth factor (FGF) and transforming growth factor (TGF). The compositions may also include an appropriate matrix, for instance, for supporting the composition and providing a surface for bone and/or cartilage growth.

The compositions may be employed in methods for treating a number of bone and/or cartilage defects, periodontal disease, and various types of wounds. These methods, according to the invention, entail administering to a patient needing such cartilage and/or bone formation, wound healing or tissue repair, an effective amount of a BMP-1 composition of the present invention. These methods may also entail the administration of a BMP-1 protein of the invention in conjunction with at least one of the novel BMP proteins disclosed in the co-owned applications described above. In addition, these methods may also include administration of a BMP-1 composition with other growth factors.

Still a further aspect of the invention are DNA sequences coding on expression for a BMP-1 protein. Such sequences include the sequence of nucleotides in a 5' to 3' direction illustrated in Tables I through III or DNA sequences which hybridize under stringent conditions with the DNA sequences of Tables I through III and encode a protein having the ability of 200 nanograms of the protein to score at least +2 in the Rosen-modified Sampath-Reddi assy of bone and/or cartilage formation described in Example III. Finally, allelic or other variations of the sequences of Tables I through III, whether such nucleotide changes result in changes in the peptide sequence or not, are also included in the present invention.

Still a further aspect of the invention is a vector containing a DNA sequence as described above in operative association with an expression control sequence therefor. Such vector may be employed in a novel process for producing a BMP-1 protein of the invention in which a cell line transformed with a DNA sequence encoding expression of a BMP-1 protein in operative association with an expression control sequence therefor, is cultured in a suitable culture medium and a BMP-1 protein is isolated and purified therefrom. This claimed process may employ a number of known cells both prokaryotic and eukaryotic as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises DNA sequence and derived amino acid sequence from a bovine BMP-1 clone bp-50, ATCC #40295. FIG. 1 corresponds to Table 1 further described below.

FIG. 2 comprises DNA sequence and derived amino acid sequence of bovine BMP-1 clone, LP-H1, ATCC #40311. FIG. 2 corresponds to Table II further described below.

FIG. 3 comprises DNA sequence and derived amino acid sequence of human BMP-1 from lambda U2OS-1, ATCC #40343. FIG. 3 corresponds to Table III further described below.

DETAILED DESCRIPTION OF THE INVENTION

The purified BMP-1 proteins of the present invention are produced by culturing a host cell transformed with a cDNA sequence substantially as shown in Table III and recovered from the culture medium. The recovered BMP-1 proteins are characterized by the 37 amino acid sequence or a substantially homologous sequence as represented by amino acids #1 through 37 of Table II. Bovine BMP-1 is characterized by such a homologous sequence as represented by amino acid #1–#37 of Table I. Some BMP-1 proteins are also characterized by the ability of 200 nanograms (ng) of the protein to score at least +2 in the Rosen-modified Sampath-Reddi assay of bone and/or cartilage formation described in Example III.

The BMP-1 proteins provided herein also include proteins encoded by the sequences similar to those of Tables I-III, but into which modifications are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of Tables I-III. These sequences, by virtue of sharing primary, secondary, or tertiary structural and conformational characteristics with BMP-1 polypeptides of Tables I–III may possess biological properties in common therewith. Thus, they may be employed as biologically active substitutes for naturally-occurring BMP-1 polypeptides in therapeutic processes.

Other specific mutations of the sequences of BMP-1 proteins described herein involve modifications of one or both of the glycosylation sites The absence of glycosylation or only partial glycosylation results from amino acid substitution or deletion at one or both of the asparagine-linked glycosylation recognition sites present in the sequences of BMP-1 shown in Tables I–III. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for BMP-1 proteins of the invention. These DNA sequences include those depicted in Tables I–III in a 5' to 3' direction and those sequences which hybridize under stringent hybridization conditions [see, T. Maniatis et al, *Molecular Cloning (A Laboratory Manual)*, Cold Spring Harbor Laboratory (1982), pages 387 to 389]to the DNA sequences of Tables I–III.

Similarly, DNA sequences which code for BMP-1 polypeptides coded for by the sequences of Tables I–III, but which differ in codon sequence due to the degeneracies of the genetic code or allelic variations (naturally-occurring base changes in the species population which may or may not result in an amino acid change) also encode the novel growth factors described herein. Variations in the DNA sequences of Tables I–III which are caused by point mutations or by induced modifications (including insertion, deletion and substitution) to enhance the activity, half-life or production of the polypeptides encoded thereby are also encompassed in the invention.

Another aspect of the present invention provides a novel method for producing BMP-1 proteins. The method of the present invention involves culturing a suitable cell line, which has been transformed with a DNA sequence coding on expression for a BMP-1 polypeptide of the invention, under the control of known regulatory sequences. Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell.* Biol. 5(7):1750–1759 (1985) or Howley et al, U.S. Pat. 4,419,446. Another suitable mammalian cell line, which is described in the accompanying examples, is the monkey COS-1 cell line. The mammalian cell line CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of these novel BMP-1 polypeptides. Preferably the vectors contain the full novel DNA sequences described above which code for the novel BMP-1 factors of the invention. Additionally the vectors also contain appropriate expression control sequences permitting expression of the BMP-1 protein sequences. Alternatively, vectors incorporating modified sequences as described above are also embodiments of the present invention and useful in the production of the BMP-1 proteins. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to one of skill in the art and may be selected depending upon the selected host cells. Such selection is routine and does not form part of the present invention.

A protein of the present invention, which induces cartilage and/or bone growth in circumstances where bone is not normally formed, has application in the healing of bone fractures and cartilage defects in humans and other animals. Such a preparation employing BMP-1 may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A BMP-1 protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and tissue repair in humans and other animals The types of wounds include burns, incisions and ulcers. (See, e.g. PCT Publication WO84/01106 for discussion of wound healing and related tissue repair.)

A further aspect of the invention is a therapeutic method and composition for repairing fractures and other conditions related to cartilage and/or bone defects or periodontal diseases. In addition, the invention comprises therapeutic methods and compositions for wound healing and tissue repair. Such compositions comprise a therapeutically effective amount of a BMP-1 protein in admixture with a pharmaceutically acceptable vehicle, carrier or matrix. It is expected that BMP-1 may act in concert with or perhaps synergistically with other related proteins and growth factors. Further therapeutic methods and compositions of the invention therefore comprise a therapeutic amount of BMP-1 with a therapeutic amount of at least one of the other BMP proteins disclosed in co-owned and concurrently filed applications as described above Further, a BMP-1 protein may be combined with other agents beneficial to the treatment of the cartilage and/or bone defect, wound or tissue in question. These agents include various growth factors such as epidermal growth factor (EGF), platelet derived growth factor (PDGF), insulin-like growth factor (IGF), and transforming growth factor (TGF). The preparation and formulation of such physiologically acceptable protein compositions, having due regard to pH, isotonicity, stability and the like, is within the skill of the art. The therapeutic compositions of the invention are also presently valuable for veterinary applications due to the lack of species specificity in BMP proteins. Particularly domestic animals and thoroughbred horses in addition to humans are desired patients for such treatment with BMP-1 proteins.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage, or other tissue damage. Topical administration may be suitable for wound healing and related tissue repair. Preferably, for bone and/or cartilage formation the composition would include a matrix capable of delivering the BMP protein to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the BMP-1 compositions will determine the appropriate formulation Potential matrices for the compositions may be biodegradable and chemically defined such as calcium sulfate, tricalciumphosphate, hydroxyapatite, polylactic acid, and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-1 protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type of BMP protein in the composition. The addition of other known growth factors, such as IGF I (insulin like growth factor I), to the final composition, may also effect the dosage. Progress can be monitored by periodic assessment of bone growth and/or repair, e.g. x-rays.

The following examples illustrate practice of the present invention in recovering and characterizing bovine BMP-1 protein and employing it to recover human BMP-1 protein, obtaining the human BMP-1 and in expressing BMP-1 via recombinant techniques.

EXAMPLE I

Isolation of Bovine Bone Inductive Factor

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171:213 (1982). After 16 to 20 hours the supernatant is removed and replaced with another 10 liters of GuCl buffer The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath-Reddi rat bone formation assay (described in Example III below) is desorbed from the column by 50 mM NaAc, 0.25 mM NaCl, 6M urea (pH 4.6). The protein from this step elution is concentrated 20- to 40- fold, then diluted 5 times with 80 mM KP04, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and/or cartilage formation activity is eluted with 100 mM $KPO_4$ (pH7.4) and 6M urea.

The protein is concentrated approximately 10 times, and solid NaCl added to a final concentration of 0.15M. This material is applied to a heparin - Sepharose column equilibrated in 50 mM $KPO_4$, 150 mM NaCl, 6M urea (pH7.4). After extensive washing of the column with starting buffer, a protein with bone and/or cartilage formation activity is eluted by 50 mM $KPO_4$, 700 mM NaCl, 6M urea (pH7.4). This fraction is concentrated to a minimum volume, and 0.4ml aliquots are applied to Superose 6 and Superose 12 columns connected in series, equilibrated with 4M GuCl, 20 mM Tris (pH7.2)

and the columns developed at a flow rate of 0.25ml/min The protein demonstrating bone and/or cartilage inductive activity has a relative migration on SDS-PAGE corresponding to an approximately 28,000 to 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active fractions are pooled and brought to pH3.0 with 10% trifluoroacetic acid (TFA). The material is applied to a 0.46×25cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active bone and/or cartilage forming material is eluted at approximately 40-44% acetonitrile. Aliquots of the appropriate active fractions are iodinated by one of the following methods: P. J. McConahey et al, *Int. Arch. Alleroy*, 29:185-189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis and urea Triton X 100 isoelectric focusing. At this stage, the protein having bone and/or cartilage forming activity is estimated to be approximately 10-50% pure.

EXAMPLE II

Characterization of Bovine Bone Inductive Factor

A. Molecular Weight

Approximately 20 ug protein from Example I is lyophilized and redissolved in 1X SDS sample buffer. After 15 minutes of heating at 37° C., the sample is applied to a 15% SDS polyacrylamide gel and then electrophoresed with cooling. The molecular weight is determined relative to prestained molecular weight standards (Bethesda Research Labs) Immediately after completion, the gel lane containing the bone and/or cartilage forming material is sliced into 0.3cm pieces. Each piece is mashed and 1.4 ml of 0.1% SDS is added. The samples are shaken gently overnight at room temperature to elute the protein. Each gel slice is desalted to prevent interference in the biological assay. The supernatant from each sample is acidified to pH 3.0 with 10% TFA, filtered through a 0.45 micron membrane and loaded on a 0.46cm×5cm C4 Vydac column developed with a gradient of 0.1% TFA to 0.1% TFA, 90% CH3CN. The appropriate bone and/or cartilage inductive protein-containing fractions are pooled and reconstituted with 20 mg rat matrix and assayed. In this gel system, the majority of bone and/or cartilage formation fractions have the mobility of a protein having a molecular weight of approximately 28,000-30,000 daltons.

B. Isoelectric Focusing

The isoelectric point of the protein having bone and/or cartilage formation activity is determined in a denaturing isoelectric focusing system. The Triton X100 urea gel system (Hoeffer Scientific) is modified as follows: 1) 40% of the ampholytes used are Servalyte 3/10; 60% are Servalyte 7-9; and 2) the catholyte used is 40 mM NaOH. Approximately 20 ug of protein from Example I is lyophilized, dissolved in sample buffer and applied to the isoelectrofocusing gel. The gel is run at 20 watts, 10° C for approximately 3 hours. At completion the lane containing bone and/or cartilage inductive factor is sliced into 0.5 cm slices. Each piece is mashed in 1.0 ml 6M urea, 5 mM Tris (pH 7.8) and the samples agitated at room temperature. The samples are acidified, filtered, desalted and assayed as described above. The major portion of activity as determined by the Rosen-modified Sampath-Reddi assay migrates in a manner consistent with a pI of about 8 8-9.2.

C. Subunit Characterization

The subunit composition of the isolated bovine bone protein is also determined Pure bone protein factor is isolated from a preparative 15% SDS gel as described above. A portion of the sample is then reduced with 5 mM DTT in sample buffer and re-electrophoresed on a 15% SDS gel. The approximately 28-30 kd protein yields two major bands at approximately 18-20 kd and approximately 16-18 kd, as well as a minor band at approximately 28-30 kd. The broadness of the two bands indicates heterogeneity caused most probably by glycosylation, other post translational modification, proteolytic degradation or carbamylation.

EXAMPLE III

Rosen Modified Sampath-Reddi Assay

A modified version of the rat bone formation assay described in Sampath and Reddi, *Proc. Natl. Acad. Sci. U.S.A.*, 80:6591-6595 (1983) is used to evaluate bone and/or cartilage activity of the bovine protein obtained in Example I and the BMP-1 proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1 % TFA, and the resulting solution added to 20 mg of rat matrix. A mock rat matrix sample not treated with the protein serves as a control. This material is frozen and lyophilized and the resulting powder enclosed in #5 gelatin capsules The capsules are implanted subcutaneously in the abdominal thoracic area of 21-49 day old male Long Evans rats. The implants are removed after 7-14 days. Half of each implant is used for alkaline phosphatase analysis [See, A. H. Reddi et al., *Proc. Natl Acad Sci.*, 69:1601 (1972)].

The other half of each implant is fixed and processed for histological analysis. About 1 glycolmethacrylate sections are stained with Von Kossa and acid fuschin to score the amount of induced bone and cartilage formation present in each implant The terms +1 through +5 represent the area of each histological section of an implant occupied by new bone and/or cartilage cells and matrix. A score of 5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

The rat matrix samples containing 200 ng of protein obtained in Example I result in bone and/or cartilage formation that filled more than 20% of the implant areas that was sectioned for histology. This protein therefore scores at least +2 in the Rosen-modified Sampath-Reddi assay. The dose response of the matrix samples indicates that the amount of bone and/or cartilage formed increases with the amount of protein in the sample. The control sample did not result in any bone and/or cartilage formation. The purity of the protein assayed is approximately 10-15% pure.

The bone and/or cartilage formed is physically confined to the space occupied by the matrix. Samples are also analyzed by SDS gel electrophoresis and isoelectric focusing as described above, followed by autoradiography. Analysis reveals a correlation of activity with protein bands at 28-30 kd and a pI of approximately 8.8-9.2. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV

Bovine BMP-1

The protein composition of Example IIA of molecular weight 28-30 kd is reduced as described in Example IIC and digested with trypsin Eight tryptic fragments are isolated by standard procedures having the following amino acid sequences:

Fragment 1: A A F L G D I A L D E E D L G
Fragment 2: A F Q V Q Q A A D L
Fragment 3: N Y Q D M V V E G
Fragment 4: S T P A Q D V S R
Fragment 5: N Q E A L R
Fragment 6: L S E P D P S H T L E E
Fragment 7: F D A Y Y
Fragment 8: L K P S N ? A T I Q S I V E Probes consisting of pools of oligonucleotides (or unique oligonucleotides) are designed according to the method of R. Lathe, J. Mol. Biol., 183 (1):1-12 (1985) and synthesized on an automated DNA synthesizer. The probes are designed from tryptic Fragment 1. One probe consists of a relatively long (32 nucleotides) "guessmer" [See J. J. Toole et al, Nature, 312:342-347 (1984)] of the following nucleotide sequence:
TCCTCATCCAGGGCAATGTCGCCCAG-GAAGGC Because the genetic code is degenerate (more than one codon can code for the same amino acid), the number of oligonucleotides in a probe pool is reduced based on the frequency of codon usage in eukaryotes, the relative stability of G:T base pairs, and the relative infrequency of the dinucleotide CpG in eukaryotic coding sequences [see Toole et al., supra.]. The second set of probes consists of shorter oligonucleotides (17 nucleotides in length) which contain all possible sequences that could encode the amino acids. The second set of probes has the following sequences:

(a) A [A/G] [A/G] TC [T/C] TC [T/C] TC [A/G] TC [T/C] AA
(b) A [A/G] [A/G] TC [T/C] TC [T/C] TC [A/G] TCNAG

Bracketed nucleotides are alternatives. "N" means either A, T, C or G.

In both cases the regions of the amino acid sequence used for probe design are chosen by avoiding highly degenerate codons where possible The oligonucleotides are synthesized on an automated DNA synthesizer; the probes are then radioactively labeled with polynucleotide kinase and $^{32}$P-ATP.

These two sets of probes are used to screen a bovine genomic recombinant library. The library is constructed as follows: Bovine liver DNA is partially digested with the restriction endonuclease enzyme Sau 3A and sedimented through a sucrose gradient. Size fractionated DNA in the range of 15-30 kb is then ligated to the bacteriophage Bam HI vector EMBL3 [Frischauf et al, J. Mol. Biol., 170:827-842 (1983)]. The library is plated at 8000 recombinants per plate. Duplicate nitrocellulose replicas of the plaques are made and amplified according to a modification of the procedure of Woo et al, Proc. Natl. Acad. Sci. USA, 75:3688-91 (1978).

The 32 mer probe is kinased with $^{32}$P-gamma-ATP and hybridized to one set of filters in 5X SSC, 0.1% SDS, 5X Denhardts, 100 ug/ml salmon sperm DNA at 45 degrees C. and washed with 5X SSC, 0.1% SDS at 45 degrees C. The 17 mer probes are kinased and hybridized to the other set of filters in 3M tetramethylammonium chloride (TMAC), 0.1M sodium phosphate pH6.5, 1 mM EDTA, 5X Denhardts, 0.6% SDS, 100 ug/ml salmon sperm DNA at 48 degrees C., and washed in 3M TMAC, 50 mM Tris pH8.0 at 50 degrees C. These conditions minimize the detection of mismatches to the 17 mer probe pool [see, Wood et al, Proc. Natl. Acad. Sci, U.S.A., 82:1585-1588 (1985)]. 400,000 recombinants are screened by this procedure and one duplicate positive is plaque purified DNA is isolated from a plate lysate of this recombinant bacteriophage designated lambda bP-50. bP-50 was deposited Dec. 16, 1986 with the American Type Culture Collection, 12301 Parklawn Drive, Rockville, Md. USA (hereinafter the "ATCC") under accession number 40295. This deposit as well as the other deposits contained herein meets the requirements of the Budapest Treaty on the International Recognition of the Deposit of Microorganisms for the Purposes of Patent Procedure and Regulations thereunder. This bp-50 clone encodes at least a portion of the bovine protein which we have designated BMP-1 or bBMP-1.

The oligonucleotide hybridizing region of this BMP-1 clone is localized to an approximately 800bp Eco RI fragment which is subcloned into M13 and sequenced by standard techniques. The partial DNA sequence and derived amino acid sequence of lambda bP-50 are shown below in Table I. The amino acid sequences corresponding to the tryptic fragments described above isolated from the bovine bone 28 to 30 kd material are underlined in Table I. The first underlined portion of the sequence corresponds to tryptic Fragment 1 above from which the oligonucleotide probes are designed The second underlined portion corresponds to tryptic Fragment 2 above. The predicted amino acid sequence indicates that tryptic Fragment 2 is preceded by a basic residue (R) as expected considering the specificity of trypsin. The nucleic acid sequence preceding the couplet CT at nucleotide positions #292-293 in Table I is presumed to be an intron (noncoding sequence) based on the presence of a consensus acceptor sequence (i.e., a pyrimidine rich tract, TCTCTCTCC, followed by AG) and the lack of a basic residue in the appropriate position of the derived amino acid sequence. The presumptive bBMP-1 peptide sequence from this genomic clone is 37 amino acids in length as depicted in Table I from amino acid #1 to amino acid #37 and is encoded by the DNA sequence from nucleotide #294 through #404 in Table I.

TABLE I

| 280 | 290 | (1) |
|---|---|---|
| CCTTGCCTCT | TCTCTCTCCA | GCT GCC TTC CTT GGG |
| | | Ala Phe Leu Gly |

TABLE I-continued

```
308                               323
GAC ATC GCC CTG GAC GAG GAG GAC TTG AGG
Asp Ile Ala Leu Asp Glu Glu Asp Leu Arg 338                               353                   368
GCC TTC CAA GTG CAG CAG GCT GCG GAC CTC AGA
Ala Phe Gln Val Gln Gln Ala Ala Asp Leu Arg 383                         398
CAG CGT GCA ACC CGC AGG TCT TCC ATC AAA GCT
Gln Arg Ala Thr Arg Arg Ser Ser Ile Lys Ala

(37)        414              424
GCA GGTACACTGG GTACAGGCCA
Ala
```

EXAMPLE V

Human BMP-1

The bovine and human BMP-1 genes are presumed to be significantly homologous, therefore the bovine BMP-1 DNA sequence of Table I (or portions thereof) is used as a probe to screen a human genomic library. The 800 bp EcoRI fragment of the bovine genomic clone is labeled with $^{32}$P by nick-translation. A human genomic library (Toole et al., supra) is plated on 20 plates at 40,000 recombinants per plate. Duplicate nitrocellulose filter replicas are made of each plate and hybridized to the nick-translated probe in 5× SSC, 5× Denhardt's, 100 ug/ml denatured salmon sperm DNA, 0.1% SDS (the standard hybridization solution) at 50 degrees centigrade for approximately 14 hours. The filters are then washed in 1× SSC, 0.1% SDS at 50 degrees centigrade and subjected to autoradiography Five duplicate positives are isolated and plaque purified. DNA is obtained from a plate lysate of one of these recombinant bacteriophage, designated LP-H1. LP-H1 was deposited with the ATCC on Mar. 6, 1987 under accession number 40311. This clone encodes at least a portion of the human genomic BMP-1 protein. The hybridizing region of LP-H1 is localized to a 2.5 kb XbaI/HindIII restriction fragment.

The partial DNA sequence and derived amino acid sequence of lambda LP-HI are shown below in Table II. The peptide sequence from this clone is 37 amino acids in length as depicted by amino acid #1 through amino acid #37 and is encoded by the DNA sequence from nucleotide #3440 through nucleotide #3550. The coding sequence of Table II is flanked by approximately 28 nucleotides (a presumptive 5' noncoding sequence) as well as approximately 19 nucleotides (a presumptive 3' noncoding sequence). A comparison of the bBMP-1 sequence of Table I with the hBMP-1 genomic sequence of Table II indicates the significant homology between the two.

Because the size of coding regions and the positions of noncoding regions is generally conserved in homologous genes of different species, the locations of the coding and noncoding regions of the BMP-1 genes may be identified. Regions of homology between the two species' genes, flanked by RNA processing signals at homologous sites, indicate a coding region.

TABLE II

```
      3419        3429         3439     (1)
CAGCCCTGGC TTCTTCTTTT CTCTTTAGCT GCC TTT
                                       Ala Phe 3454                         3469
CTT GGG GAC ATT GCC CTG GAC GAA GAG GAC CTG
Leu Gly Asp Ile Ala Leu Asp Glu Glu Asp Leu 3484                     3499
AGG GCC TTC CAG GTA CAG CAG GCT GTG GAT CTC
Arg Ala Phe Gln Val Gln Gln Ala Val Asp Leu 3514                3529                      3544
AGA CGG CAC ACA GCT CGT AAG TCC TCC ATC AAA
Arg Arg His Thr Ala Arg Lys Ser Ser Ile Lys

(37)          3560          3570
GCT GCA GGTAAGCCGG GTGCCAATGG
Ala Ala
```

A probe specific for the human coding sequence given in Table II is used to identify a human cell line or tissue which synthesizes BMP-1. The probe is made according to the following method. Two oligonucleotides having the following sequences:

(a) GGGAATTCTGCCTTTCTTGG-GGACATTGCCCTGGACGAAGAGGACCT-GAG (b) CGGGATCCGTCTGAGATC-CACAGCCTGCTGTACCTGGAAGGCCCT-CAGG are synthesized on an automated synthesizer, annealed, extended using the Klenow fragment of E. coli DNA polymerase I, digested with the restriction enzymes Eco RI and Bam HI, and inserted into an M13 vector. A single-stranded $^{32}$P-labeled probe is then made off a template preparation of this subclone by standard techniques. Polyadenylated RNAs from various cell and tissue sources are electrophoresed on formaldehyde-agarose gels and transferred to nitrocellulose by the method of Toole et al., supra. The probe is then hybridized to the nitrocellulose blot in 50% formamide, 5×SSC, 0.1% SDS, 40 mM sodium phosphate pH 6.5, 100 ug/ml denatured salmon sperm DNA, and 5 mM vanadyl ribonucleosides at 42° C. overnight and washed at 65° C. in 0.2×SSC, 0.1% SDS. Following autoradiography, the lane containing RNA from the human osteosarcoma cell line U-2 OS contains hybridizing bands corresponding to RNA species of approximately 4.3 and 3.0 kb.

cDNA is synthesized from U-2 OS polyadenylated RNA and cloned into lambda gt10 by established techniques (Toole et al., supra). 20,000 recombinants from this library are plated on each of 50 plates. Duplicate nitrocellulose replicas are made of the plates. The above described oligonucleotides are kinased with $^{32}$P-gamma-ATP and hybridized to the two sets of replicas at 55° centigrade in standard hybridization solution overnight. The filters are then washed in 1×SSC, 0.1% SDS at 55° centigrade and subjected to autoradiography. One duplicate positive, designated lambda U20S-1, is plaque purified. Lambda U20S-1 was deposited with the ATCC on Jun. 16, 1987 under accession number 40343.

The entire nucleotide sequence and derived amino acid sequence of the insert of lambda U2OS-1 is given in Table III. This cDNA clone encodes a Met followed by a hydrophobic leader sequence characteristic of a secreted protein, and contains a stop codon at nucleotide positions #2226–190 2228. This clone contains an open reading frame of 2190 bp, encoding a protein of 730 amino acids with a molecular weight of approximately 83kd based on this amino acid sequence. The clone contains sequence identical to the coding region given in Table II. Amino acids #51 to #87 of Table III correspond to amino acids #1 to #37 of Table II. The BMP-1 protein encoded by the sequence of Table III is contemplated to contain this 37 amino acid sequence or a sequence substantially homologous thereto. The amino acid sequence of Table III is contemplated to represent a primary translation product which is cleaved upon secretion to produce the human BMP-1 protein. It is contemplated that BMP-1 corresponds to the approximately 28-30 kd subunit of Example IIC. This clone is therefore a cDNA for human BMP-1 corresponding to the human gene fragment contained in the genomic hBMP-1 sequence lambda LP-H1. It is noted that amino acids #550 to #590 of BMP-1 as shown in Table III are homologous to epidermal growth factor and the "growth factor" domains of various proteins such as Protein C, Factor X and Factor IX.

A comparison of the BMP-1 amino acid sequence of Table III with itself indicates that there are three regions of internal sequence similarity, defining three additional domains. Each block of sequence is 113 amino acid residues long; the first two are tandemly repeated (residues 322-434 and 435-547), the third (591-703) follows the growth factor domain An alignment of these three sequences shows that in each block there are four absolutely conserved cys residues, suggesting a common secondary conformation for these domains.

TABLE III

```
         10           20          30        (1)         50                    65
CTAGAGGCCG CTTCCCTCGC CGCCGCCCCG CCAGC ATG CCC GGC GTG GCC CGC CTG CCG CTG CTG CTC
                                       MET Pro Gly Val Ala Arg Leu Pro Leu Leu Leu 80                    95                110                125
GGG CTG CTG CTG CTC CCG CGT CCC GGC CGG CCG CTG GAC TTG GCC GAC TAC ACC TAT GAC CTG GCG
Gly Leu Leu Leu Leu Pro Arg Pro Gly Arg Pro Leu Asp Leu Ala Asp Tyr Thr Tyr Asp Leu Ala 140                   155               170                185  (51)             200
GAG GAG GAC GAC TCG GAG CCC CTC AAC TAC AAA GAC CCC TGC AAG GCG GCT GCC TTT CTT GGG GAC
Glu Glu Asp Asp Ser Glu Pro Leu Asn Tyr Lys Asp Pro Cys Lys Ala Ala Ala Phe Leu Gly Asp 215                    230                245                260
ATT GCC CTG GAC GAA GAG GAC CTG AGG GCC TTC CAG GTA CAG CAG GCT GTG GAT CTC AGA CGG CAC
Ile Ala Leu Asp Glu Glu Asp Leu Arg Ala Phe Gln Val Gln Gln Ala Val Asp Leu Arg Arg His 275                   290         (87)    305                    320
ACA GCT CGT AAG TCC TCC ATC AAA GCT GCA GTT CCA GGA AAC ACT TCT ACC CCC AGC TGC CAG AGC
Thr Ala Arg Lys Ser Ser Ile Lys Ala Ala Val Pro Gly Asn Thr Ser Thr Pro Ser Cys Gln Ser 335                   350                   365                  380                   395
ACC AAC GGG CAG CCT CAG AGG GGA GCC TGT GGG AGA TGG AGA GGT AGA TCC GTA GCC GGC GGC GCG
Thr Asn Gly Gln Pro Gln Arg Gly Ala Cys Gly Arg Trp Arg Gly Arg Ser Arg Ser Arg Arg Ala 410                   425                 440                   455
GCG ACG TCC CGA CCA GAG CGT GTG TGG CCC GAT GGG GTC ATC CCC TTT GTC ATT GGG GGA AAC TTC
Ala Thr Ser Arg Pro Glu Arg Val Trp Pro Asp Gly Val Ile Pro Phe Val Ile Gly Gly Asn Phe 470                   485                 500                   515                530
ACT GGT AGC CAG AGG GCA GTC TTC CGG CAG GCC ATG AGG CAC TGG GAG AAG CAC ACC TGT GTC ACC
Thr Gly Ser Gln Arg Ala Val Phe Arg Gln Ala MET Arg His Trp Glu Lys His Thr Cys Val Thr 545                   560                  575                   590
TTC CTG GAG CGC ACT GAC GAG GAC AGC TAT ATT GTG TTC ACC TAT CGA CCT TGC GGG TGC TGC TCC
Phe Leu Glu Arg Thr Asp Glu Asp Ser Tyr Ile Val Phe Thr Tyr Arg Pro Cys Gly Cys Cys Ser 605                   620                   635                  650
TAC GTG GGT CGC CGC GGC GGG GGC CCC CAG GCC ATC TCC ATC GGC AAG AAC TGT GAC AAG TTC GGC
Tyr Val Gly Arg Arg Gly Gly Gly Pro Gln Ala Ile Ser Ile Gly Lys Asn Cys Asp Lys Phe Gly 665                   680                   695                  710                   725
ATT GTG GTC CAC GAG CTG GGC CAC GTC GTC GGC TTC TGG CAC GAA CAC ACT CGG CCA GAC CGG GAC
Ile Val Val His Glu Leu Gly His Val Val Gly Phe Trp His Glu His Thr Arg Pro Asp Arg Asp 740                   755                 770                   785
CGC CAC GTT TCC ATC GTT CGT GAG AAC ATC CAG CCA GGG CAG GAG TAT AAC TTC CTG AAG ATG GAG
Arg His Val Ser Ile Val Arg Glu Asn Ile Gln Pro Gly Gln Glu Tyr Asn Phe Leu Lys MET Glu 800                   815                   830                  845                 860
CCT CAG GAG GTG GAG TCC CTG GGG GAG ACC TAT GAC TTC GAC AGC ATC ATG CAT TAC GCT CGG AAC
Pro Gln Glu Val Glu Ser Leu Gly Glu Thr Tyr Asp Phe Asp Ser Ile MET His Tyr Ala Arg Asn 875                   890                   905                   920
ACA TTC TCC AGG GGC ATC TTC CTG GAT ACC ATT GTC CCC AAG TAT GAG GTG AAC GGG GTG AAA CCT
Thr Phe Ser Arg Gly Ile Phe Leu Asp Thr Ile Val Pro Lys Tyr Glu Val Asn Gly Val Lys Pro 935                    950                   965                   980
CCC ATT GGC CAA AGG ACA CGG CTC AGC AAG GGG GAC ATT GCC CAA GCC CGC AAG CTT TAC AAG TGC
Pro Ile Gly Gln Arg Thr Arg Leu Ser Lys Gly Asp Ile Ala Gln Ala Arg Lys Leu Tyr Lys Cys 995                   1010                  1025                  1040                  1055
CCA GCC TGT GGA GAG ACC CTG CAA GAC AGC ACA GGC AAC TTC TCC TCC CCT GAA TAC CCC AAT GGC
Pro Ala Cys Gly Glu Thr Leu Gln Asp Ser Thr Gly Asn Phe Ser Ser Pro Glu Tyr Pro Asn Gly
```

TABLE III-continued

```
         1070                1085                1100                1115
TAC TCT GCT CAC ATG CAC TGC GTG TGG CGC ATC TCT GTC ACA CCC GGG GAG AAG ATC ATC CTG AAC
Tyr Ser Ala His MET His Cys Val Trp Arg Ile Ser Val Thr Pro Gly Glu Lys Ile Ile Leu Asn 1130                1145                1160                1175            1190
TTC ACG TCC CTG GAC CTG TAC CGC AGC CGC CTG TGC TGG TAC GAC TAT GTG GAG GTC CGA GAT GGC
Phe Thr Ser Leu Asp Leu Tyr Arg Ser Arg Leu Cys Trp Tyr Asp Tyr Val Glu Val Arg Asp Gly 1205                1220                1235                1250
TTC TGG AGG AAG GCG CCC CTC CGA GGC CGC TTC TGC GGG TCC AAA CTC CCT GAG CCT ATC GTC TCC
Phe Trp Arg Lys Ala Pro Leu Arg Gly Arg Phe Cys Gly Ser Lys Leu Pro Glu Pro Ile Val Ser 1265                1280                1295                1310
ACT GAC AGC CGC CTC TGG GTT GAA TTC CGC AGC AGC AGC AAT TGG GTT GGA AAG GGC TTC TTT GCA
Thr Asp Ser Arg Leu Trp Val Glu Phe Arg Ser Ser Ser Asn Trp Val Gly Lys Gly Phe Phe Ala 1325                1340                1355                1370                1385
GTC TAC GAA GCC ATC TGC GGG GGT GAT GTG AAA AAG GAC TAT GGC CAC ATT CAA TCG CCC AAC TAC
Val Tyr Glu Ala Ile Cys Gly Gly Asp Val Lys Lys Asp Tyr Gly His Ile Gln Ser Pro Asn Tyr 1400                1415                1430                1445
CCA GAC GAT TAC CGG CCC AGC AAA GTC TGC ATC TGG CGG ATC CAG GTG TCT GAG GGC TTC CAC GTG
Pro Asp Asp Tyr Arg Pro Ser Lys Val Cys Ile Trp Arg Ile Gln Val Ser Glu Gly Phe His Val 1460                1475                1490                1505            1520
GGC CTC ACA TTC CAG TCC TTT GAG ATT GAG CGC CAC GAC AGC TGT GCC TAC GAC TAT CTG GAG GTG
Gly Leu Thr Phe Gln Ser Phe Glu Ile Glu Arg His Asp Ser Cys Ala Tyr Asp Tyr Leu Glu Val 1535                1550                1565                1580
CGC GAC GGG CAC AGT GAG AGC AGC ACC CTC ATC GGG CGC TAC TGT GGC TAT GAG AAG CCT GAT GAC
Arg Asp Gly His Ser Glu Ser Ser Thr Leu Ile Gly Arg Tyr Cys Gly Tyr Glu Lys Pro Asp Asp 1595                1610                1625                1640
ATC AAG AGC ACG TCC AGC CGC CTC TGG CTC AAG TTC GTC TCT GAC GGG TCC ATT AAC AAA GCG GGC
Ile Lys Ser Thr Ser Ser Arg Leu Trp Leu Lys Phe Val Ser Asp Gly Ser Ile Asn Lys Ala Gly 1655                1670                1685                1700                1715
TTT GCC GTC AAC TTT TTC AAA GAG GTG GAC GAG TGC TCT CGG CCC AAC CGC GGG GGC TGT GAG CAG
Phe Ala Val Asn Phe Phe Lys Glu Val Asp Glu Cys Ser Arg Pro Asn Arg Gly Gly Cys Glu Gln 1730                1745                1760                1775
CGG TGC CTC AAC ACC CTG GGC AGC TAC AAG TGC AGC TGT GAC CCC GGG TAC GAG CTG GCC CCA GAC
Arg Cys Leu Asn Thr Leu Gly Ser Tyr Lys Cys Ser Cys Asp Pro Gly Tyr Glu Leu Ala Pro Asp 1790                1805                1820                1835            1850
AAG CGC CGC TGT GAG GCT CGT TGT GGC GGA TTC CTC ACC AAG CTC AAC GGC TCC ATC ACC AGC CCG
Lys Arg Arg Cys Glu Ala Arg Cys Gly Gly Phe Leu Thr Lys Leu Asn Gly Ser Ile Thr Ser Pro 1865                1880                1895                1910
GGC TGG CCC AAG GAG TAC CCC CCC AAC AAG AAC TGC ATC TGG CAG CTG GTG GCC CCC ACC CAG TAC
Gly Trp Pro Lys Glu Tyr Pro Pro Asn Lys Asn Cys Ile Trp Gln Leu Val Ala Pro Thr Gln Tyr 1925                1940                1955                1970
CGC ATC TCC CTG CAG TTT GAC TTC TTT GAG ACA GAG GGC AAT GAT GTG TGC AAG TAC GAC TTC GTG
Arg Ile Ser Leu Gln Phe Asp Phe Phe Glu Thr Glu Gly Asn Asp Val Cys Lys Tyr Asp Phe Val 1985                2000                2015                2030                 2045
GAG GTG CGC AGT GGA CTC ACA GCT GAC TCC AAG CTG CAT GGC AAG TTC TGT GGT TCT GAG AAG CCC
Glu Val Arg Ser Gly Leu Thr Ala Asp Ser Lys Leu His Gly Lys Phe Cys Gly Ser Glu Lys Pro 2060                2075                2090                2105
GAG GTC ATC ACC TCC CAG TAC AAC AAC ATG CGC GTG GAG TTC AAG TCC GAC AAC ACC GTG TCC AAA
Glu Val Ile Thr Ser Gln Tyr Asn Asn MET Arg Val Glu Phe Lys Ser Asp Asn Thr Val Ser Lys 2120                2135                2150                2165                2180
AAG GGC TTC AAG GCC CAC TTC TTC TCA GAA AAG AGG CCA GCT CTG CAG CCC CCT CGG GGA CGC CCC
Lys Gly Phe Lys Ala His Phe Phe Ser Glu Lys Arg Pro Ala Leu Gln Pro Pro Arg Gly Arg Pro (730)
           2195                2210                2225            2235            2245
CAC CAG CTC AAA TTC CGA GTG CAG AAA AGA AAC CGG ACC CCC CAG TGAGGCCTGC CAGGCCTCCC
His Gln Leu Lys Phe Arg Val Gln Lys Arg Asn Arg Thr Pro Gln 2255       2265       2275       2285       2295       2305       2315
GGACCCCTTG TTACTCAGGA ACCTCACCTT GGACGGAATG GGATGGGGGC TTCGGTGCCC ACCAACCCCC 2325       2335       2345       2355       2365       2375       2385
CACCTCCACT CTGCCATTCC GGCCCACCTC CCTCTGGCCG GACAGAACTG GTGCTCTCTT CTCCCCACTG
```

TABLE III-continued

|  2395 | 2405 | 2415 | 2425 | 2435 | 2445 | 2455 |
|---|---|---|---|---|---|---|
| TGCCCGTCCG | CGGACCGGGG | ACCCTTCCCC | GTGCCCTACC | CCCTCCCATT | TTGATGGTGT | CTGTGACATT |

| 2465 | 2475 | 2485 | 2495 | | | |
|---|---|---|---|---|---|---|
| TCCTGTTGTG | AAGTAAAAGA | GGGACCCCTG | CGTCCTGCCT | CTAGA | | |

EXAMPLE VI
Expression of BMP-1

In order to produce bovine, human or other mammalian BMP-1 proteins, the DNA encoding BMP-1 is transferred into an appropriate expression vector and introduced into mammalian cells or other preferred eukaryotic or prokaryotic hosts by conventional genetic engineering techniques. However the presently preferred expression system for biologically active recombinant human BMP-1 is stably transformed mammalian cells.

One skilled in the art can construct mammalian expression vectors by employing the sequence of Tables I-III or other modified sequences and known vectors, such as pCD [Okayama et al., *Mol. Cell Biol.*, 2:161-170 (1982)] and pJL3, pJL4 [Gough et al., *EMBO J.*, 4:645-653 (1985)]. The transformation of these vectors into appropriate host cells can result in expression of BMP-1. One skilled in the art may manipulate the sequences of Tables I-III by eliminating or replacing the mammalian regulatory sequences flanking the coding sequence with bacterial sequences to create bacterial vectors for intracellular or extracellular expression by bacterial cells. For example, the coding sequences may be further manipulated (e.g. ligated to other known linkers or modified by deleting non-coding sequences therefrom or altering nucleotides therein by other known techniques). The modified BMP-1 coding sequence may then be inserted into a known bacterial vector using procedures such as described in T. Taniguchi et al., *Proc. Natl Acad. Sci. USA*, 77:5230-5233 (1980). This exemplary bacterial vector may then be transformed into bacterial host cells and BMP-1 expressed thereby For a strategy for producing extracellular expression of BMP-1 in bacterial cells., see, e.g. European patent application EPA 177,343.

Similar manipulations may be performed for the construction of an insect vector [See, e.g. procedures described in published European patent application 155,476] for expression in insect cells A yeast vector may also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-1 protein of the invention from mammalian cells involves the construction of cells containing multiple copies of the heterologous BMP-1 gene. The heterologous gene can be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601-629 (1982). This approach can be employed with a number of different cell types. For example, a plasmid containing a DNA sequence for a BMP-1 protein of the invention in operative association with other plasmid sequences enabling expression thereof and the DHFR expression plasmid pAdA26SV-(A)3 [Kaufman and Sharp, *Mol. Cell. Biol.*, 2:1304 (1982)] can be co-introduced into DHFR-deficient CHO cells, DUKX-BII, by calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., *Mol Cell Biol.*, 5:1750 (1983). Transformants are cloned, and biologically active BMP-1 expression is monitored by the Rosen-modified Sampath-Reddi rat bone formation assay described above in Example III. BMP-1 expression should increase with increasing levels of MTX resistance. Similar procedures can be followed to produce other BMP-1 family proteins.

As one specific example, to produce a human BMP-1 protein, the insert of U20S-1 is released from the vector arms by digestion with Sal I and subcloned into the mammalian expression vector pMT2CX digested with Xho I. Plasmid DNA from this subclone is transfected into COS cells by the DEAE-dextran procedure [Sompayrac and Danna *PNAS* 78:7575-7578 (1981); Luthman and Magnusson, *Nucl.Acids Res.* 11: 1295-1308 (1983)] and the cells are cultured. Serum-free 24 hr. conditioned medium supernatant is collected from the cells starting 40-70 hr. post-transfection.

The mammalian expression vector pMT2 Cla-Xho (pMT2 CX) is a derivative of p91023 (b) (Wong et al., Science 228:810-815, 1985) differing from the latter in that it contains the ampicillin resistance gene in place of the tetracycline resistance gene and further contains a XhoI site for insertion of cDNA clones. The functional elements of pMT2 Cla-Xho have been described (Kaufman, R. J., 1985, Proc. Natl. Acad. Sci. USA 82:689-693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in *E. coli*.

Plasmid pMT2 Cla-Xho is obtained by EcoRI digestion of pMT2-VWF, which has been deposited with the (ATCC) under accession number ATCC 67122. EcoRI digestion excises the cDNA insert present in pMT2-VWF, yielding pMT2 in linear form which can be ligated and used to transform *E. coli* HB 101 or DH-5 to ampicillin resistance. Plasmid pMT2 DNA can be prepared by conventional methods. pMT2CX is then constructed by digesting pMT2 with Eco RV and XbaI, treating the digested DNA with Klenow fragment of DNA polymerase I, and ligating Cla linkers (NEBiolabs, CATCGATG). This removes bases 2266 to 2421 starting from the Hind III site near the SV40 origin of replication and enhancer sequences of pMT2. Plasmid DNA is then digested with EcoRI, blunted as above, and ligated to an EcoRI adapter,

```
5' PO4—AATTCCTCGAGAGCT 3'
       3' GGAGCTCTCGA 5'
``` digested with XhoI, and ligated, yielding pMT2 Cla-Xho, which may then be used to transform *E. coli* to ampicillin resistance. Plasmid pMT2 Cla-Xho DNA may be prepared by conventional methods.

Example VII

Biological Activity of Expressed BMP-1

To measure the biological activity of the expressed BMP-1 obtained in Example VI above, the BMP-1 is partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15 M NaCl, pH 7.4 (starting buffer). This material is then applied to a 1.1 ml Heparin Sepharose column in starting buffer. Unbound proteins are removed by an 8 ml wash of starting buffer, and bound proteins, including BMP-1, are desorbed by a 3-4 ml wash of 20 mM Tris, 2.0 M NaCl, pH 7.4.

The proteins bound by the Heparin column are concentrated approximately 10-fold on a Centricon 10 and the salt reduced by diafiltration with 0.1% trifluoroacetic acid. Purified BMP-1 is approximately 95% substantially free from other proteinaceous materials. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-1 have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Addition of human BMP-1 to the matrix material resulted in formation of cartilage-like nodules at 7 days post implantation. The chondroblast-type cells were recognizable by shape and expression of metachromatic matrix. The assay results indicate that approximately 200 ng of BMP-1 results in a score of at least +2. The amount of activity observed for BMP-1 indicates that it may be dependent on the amount of BMP-1 added to the matrix sample.

Similar levels of activity are seen in the Heparin Sepharose fractionated COS cell extracts. Partial purification is accomplished in a similar manner as described above except that 6 M urea is included in all the buffers.

The procedures described above may be employed to isolate other related BMP-1 factors of interest by utilizing the bovine BMP-1 or human BMP-1 as a probe source. Such other BMP-1 proteins may find similar utility in, inter alia, fracture repair, wound healing, and tissue repair The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An isolated encoding a BMP-1 protein.

2. A host cell transformed with a DNA of claim 1.

3. An isolated DNA encoding a BMP-1 protein which is characterized by the ability to induce the formation of bone and/or cartilage said DNA comprising a coding sequence selected from the group consisting of:

(a) nucleotide #294 through nucleotide #404 of FIG. 1;
  (b) nucleotide #3440 through nucleotide #3550 of FIG. 2;
  (c) nucleotide #36 through nucleotide #2225 of FIG. 3; and
  (d) naturally occurring allelic sequences and equivalent degenerative codon sequences of (a), (b), and (c).

4. A vector comprising a DNA of claim 3 in operative association with an expression control sequence therfor.

5. A host cell transformed with a vector of claim 4.

6. An isolated DNA encoding a BMP-1 protein said DNA comprising nucleotide #36 through nucleotide #2225 of FIG. 3.

7. A vector comprising the DNA of claim 6.

8. A host cell transformed with vector of claim 7.

* * * * *